US005712453A

United States Patent [19]

Bungardt et al.

[11] Patent Number: 5,712,453

[45] Date of Patent: Jan. 27, 1998

[54] CONCHA HEADSET STABILIZER

[75] Inventors: Gabriele Bungardt, Aptos, Calif.; Luis Pedraza, Hyde Park; Betsy Goodrich, Roslindale, both of Mass.; Edmund J. Morrissey, III, Aptos, Calif.

[73] Assignee: Plantronics, Inc., Santa Cruz, Calif.

[21] Appl. No.: 420,241

[22] Filed: Apr. 11, 1995

Related U.S. Application Data

[63] Continuation of Ser. No. 234,302, Apr. 28, 1994, abandoned.

[51] Int. Cl.[6] ........ A61B 7/02

[52] U.S. Cl. ........ 181/135; 381/187

[58] Field of Search ........ 181/129, 130, 181/135, 137; 381/183, 187, 68.6, 69

[56] References Cited

U.S. PATENT DOCUMENTS

| | | | |
|---|---|---|---|
| 1,614,987 | 1/1927 | Langenbeck et al. | 181/135 |
| 1,668,910 | 5/1928 | Jones | 181/135 |
| 1,893,143 | 1/1933 | Koch | 181/135 |
| 1,953,437 | 4/1934 | Schier | 181/135 |
| 3,041,856 | 7/1962 | Neal | 181/135 |
| 4,429,194 | 1/1984 | Kamon et al. . | |
| 5,142,587 | 8/1992 | Kobayashi | 181/129 |
| 5,260,997 | 11/1993 | Gattey et al. . | |

FOREIGN PATENT DOCUMENTS

| | | |
|---|---|---|
| 0421681 | 4/1991 | European Pat. Off. . |
| 353758 | 5/1922 | Germany . |
| 3328100.9 | 7/1984 | Germany . |

*Primary Examiner*—Khanh Dang
*Attorney, Agent, or Firm*—Fenwick & West LLP

[57] ABSTRACT

An apparatus for stabilizing a concha style headset comprises a receiver attachment that couples to the body of the receiver of the headset, a flexible and resilient support member extending from the receiver attachment, and a concha stabilizer pad coupled to the end of the support member, such that the concha stabilizer pad contacts the upper concha under the antihelix of the ear with the receiver placed in the lower concha in front of the ear canal. The receiver attachment can include a foam ear cushion that covers the portion of the receiver that is placed in the lower concha, with the concha stabilizer pad and the flexible support member formed of a compressed cellular foam. Support ribs extend from the upper surface of the ear cushion along the surface of the support member and join the concha stabilizer pad. Alternatively, the receiver attachment can include retaining members that engage in mounting holes in the receiver, and may include curved members which wrap around the body of the receiver when the retaining members mount the underside of the receiver. The support member can then include a flexible arch or stalk, with the concha stabilizer pad (or torus) located at the top of the arch.

15 Claims, 3 Drawing Sheets

CONCHA HEADSET STABILIZER

This is a continuation of application Ser. No. 08/234,302 filed on Apr. 28, 1994, now abandoned.

BACKGROUND OF THE INVENTION

1. Field of Invention

The invention relates generally to the design of headsets, and more particularly, to an apparatus for stabilizing such headsets.

2. Description of the Background Art

A concha style headset is a device for transmitting received sounds to the ear of the user by means of a small receiver which is sized to fit in the lower concha in front of the ear canal. In telecommunication headsets, a tubular extension or a voice tube is often coupled to the receiver and extends down and towards the user's mouth for receiving the user's voice and transmitting it over a telecommunications line. Conventional earbud concha style headsets position the receiver inside the lower concha between the tragus and anti-tragus to establish placement and support on the ear. However, different ear shapes and sizes make it difficult for a single design to both fit the ear correctly and to stabilize the headset. Accordingly, the receiver is typically held in place by mechanical devices which fit around the outside of the ear, or around the head. These device, s add mechanical complexity, which decreases ease of use, and increases the cost of manufacturing. Mechanical stabilizers also increase the size and weight of the headset, resulting in increased fatigue from prolonged use.

One example of such mechanical stabilizers is the ear hook. An ear hook is a large semicircular component that fits around the top of the ear between the helix and the side of the head. The receiver is then attached to the body of the ear hook, and held in the lower concha in front of the ear canal, or it can be coupled to the receiver with a flexible tube and placed into the lower concha. The ear hook presents three disadvantages. First, an ear hook is awkward and time consuming to place on the ear because of the need to manually position the ear hook. Second, the ear hook does not ensure that the receiver stays in front of the ear canal, resulting in the user having to periodically readjust the ear hook or receiver during usage to correct the placement. Finally, the ear hook requires additional mechanical parts, such as those for adjusting for left and right ears, and different ear sizes. The ear hook and such pans add weight to the headset, increasing fatigue during use, and increasing manufacturing and product costs.

Another common alternative is a headband style headset that locates the receiver in front of the ear canal using a stiff metal band which arches over the top of the head from ear to ear. The headband adds weight and mechanical complexity to the headset, requires both hands to put on and take off, and can take some time to adjust properly.

It would be desirable therefore, to provide an apparatus for stabilizing a concha headset that overcomes the disadvantages of the prior art. In particular, it is desirable to provide a means for stabilizing the headset that adds little weight or mechanical complexity to the headset, thereby reducing manufacturing costs, and increasing usability, and adaptability to existing headsets.

SUMMARY OF INVENTION

A stabilizer for a headset comprises a receiver attachment which couples to the receiver, and a concha stabilizer pad Which is secured to the receiver attachment by a flexible supporting member. The concha stabilizer pad engages the upper concha below the antihelix when the receiver is placed in the lower concha between the tragus and antitragus, thereby creating three points of contact at the tragus, the anti-tragus, and the upper concha.

One embodiment of the stabilizer comprises a shaped foam piece which couples onto the receiver of a headset. A portion of the foam piece forms an ear cushion that covers the receiver, and fits between the tragus and the antitragus. Another portion of the foam piece forms a supporting foam member that extends from the top of the ear cushion to a concha stabilizer pad that rests against the upper concha. The supporting member is elongated and flexible, providing a spring hinge-like action which automatically adjusts the stabilizer to the size and shape of the upper concha, while providing sufficient force to hold the receiver against the lower concha.

Alternatively, the stabilizer is formed from an arch that connects to a receiver, and is disposed upward from the receiver. A concha stabilizer pad is secured to the top of the arch and provides a contact point when inserted into the upper concha. The arch is resilient to provide tension to the upper concha through the foam pad, thereby stabilizing the receiver in the ear. The resilient arch can be formed of wire, an elastomeric compound, or the like. In another alternate embodiment the stabilizer is formed as a torus (ring shape) that is coupled to a stalk shaped supporting member.

The simple design and absence of mechanical parts results in several benefits. The concha stabilizer permits fast and easy one-handed insertion and removal, without the need for repeated adjustment. The concha stabilizer maintains the receiver in the lower concha, ensuring proper placement and eliminating the need for frequent readjustment. The concha stabilizer is self-adjusting with no additional mechanical parts, and is symmetrical for either ear. The small form factor increases wearability, and decreases fatigue. Further, manufacturing costs are also reduced. The design of the concha stabilizer is readily adaptable and applicable to a variety of existing headsets which use an ear cushion, thereby allowing use of the present invention with no need for redesign.

DESCRIPTION OF THE PREFERRED EMBODIMENT

The present invention for stabilizing a concha style headset includes a receiver attachment that couples to the receiver, a flexible stabilizer support member that couples to the receiver attachment and extends away from the receiver attachment and toward the upper concha with the receiver placed in the ear, and a concha stabilizer pad mounted at the end or top of the support member, for contacting the upper concha below the antihelix.

Figure 1A:
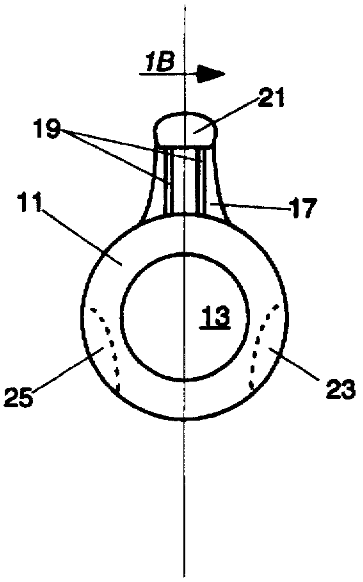
FIGS. 1A and 1B show a side and a cross-sectional view of the concha stabilizer.
Figure 1B:
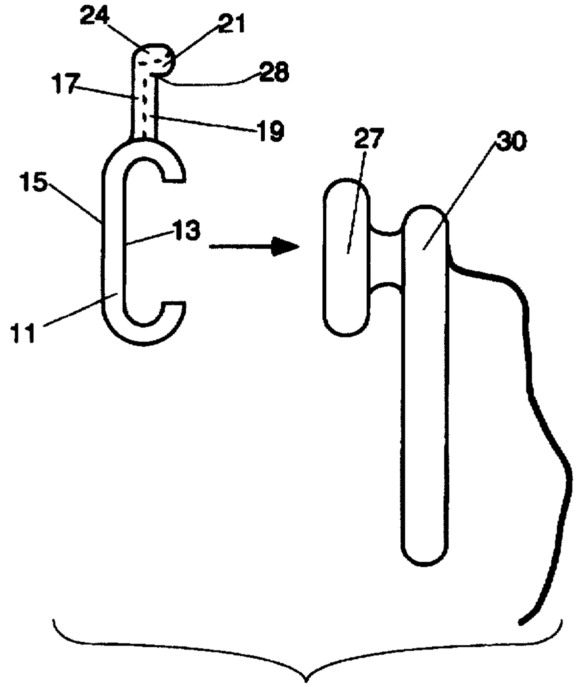

FIGS. 1A and 1B show an embodiment of the invention for stabilizing a concha style headset typically including a receiver 27 and a voice tube 30. A receiver attachment comprises an ear cushion 11 preferably dimensioned as an oblate spheroid, formed of a reticulated, fully open-pore flexible, ester type polyurethane foam. A suitable foam is the P100 foam commercially available from Illbruck Inc.. The foam has a density of approximately 1.75 lbs/ft$^3$, provides a minimum restriction to air flow, and is functionally transparent to the transmission of sound from the receiver 27. The ear cushion 11 has an open central recessed portion 13 forming a "C" shape, which is dimensioned to fit snugly onto the receiver 27. When placed into the lower concha 41 (FIG. 3), the ear cushion 11 contacts the tragus 35 and the antitragus 39 at a tragus contact point 23 and an antitragus contact point 25, respectively, where the face 15 of the ear cushion 11 rests in the lower concha 41 and faces toward the ear canal 33. The left/right orientation of the tragus contact point 23 and the antitragus contact point 25 with respect to the face 15 of the ear cushion 11 is reversed for the left and right ears.

Extending from the upper surface of the ear cushion 11 is a flexible support member, here a stabilizer support 17. The stabilizer support 17 is an open cell foam which has been compressed to become sufficiently rigid to provide both flexibility for, and resistance to, positional deformation. The foam can be the same as that used for the ear cushion, compressed approximately 1.74:1 using conventional techniques, yielding an approximate effective density of 9.29 lbs/ft$^3$. The end of the stabilizer support 17 is coupled to a concha stabilizer pad 21 which contacts the upper concha 43 beneath the antihelix 45. The concha stabilizer pad 21 is preferably ellipsoid in shape and is formed of the same compressed open cell foam as the stabilizer support 17. The stabilizer support 17 can have a uniform width or can taper from the ear cushion 11 toward the concha stabilizer pad 21. Two support ribs 19 are disposed longitudinally along the inner surface of the stabilizer support 17 and extend from the upper surface of the ear cushion 11 to the underside of the concha stabilizer pad 21 to increase the rigidity and durability of the stabilizer support 17. The longitudinal axis of stabilizer support 17 aligns with the longitudinal axis of the voice tube 30. The stabilizer support 17 can be formed out of non-compressed open cell foam if the foam is overmolded to a more rigid material like wire or plastic.

During use, the ear cushion 11 is placed into the lower concha 41, firing into the intertragic notch 37 between the tragus 35 and the antitragus 39, with the contact points 23, 25 respectively engaged. The user then pushes the stabilizer support 17 into and against the upper concha 43, below the antihelix 45. The outer surface of the concha stabilizer pad 21 provides a concha contact point 24 which contacts the upper concha 43, thereby providing three points of contact for stabilizing the ear cushion 11. The placement action causes the stabilizer support 17 to form a hinge point 28 where the underside of the concha stabilizer pad 21 joins the support rib 19. The cellular foam of the stabilizer support 17 gives the hinge point 28 sufficient angular tension to maintain the concha contact point 24 against the surface of the upper concha 43. The degree of angular flexure of the hinge point 28 is dependent upon the size and shape of the user's ear, particularly the upper concha 43, antihelix 45, and the crux of the helix 31. The hinge action of the hinge point 28, coupled with the general flexibility and resilience of the stabilizer support 17, allows the stabilizer support 17 to automatically adjust to the size and shape of the user's upper concha 43 without any additional mechanical devices, to properly position the concha stabilizer pad 21.

Figure 2A:
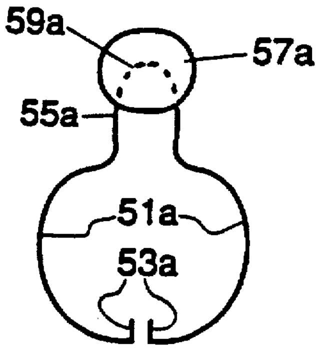
FIGS. 2A, 2B, and 2C are illustrations of alternate embodiments of a concha stabilizer.
Figure 2B:
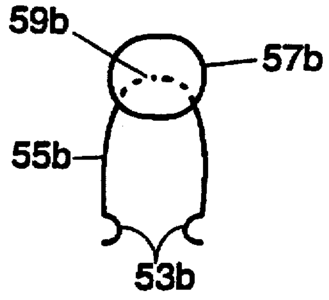
Figure 2C:
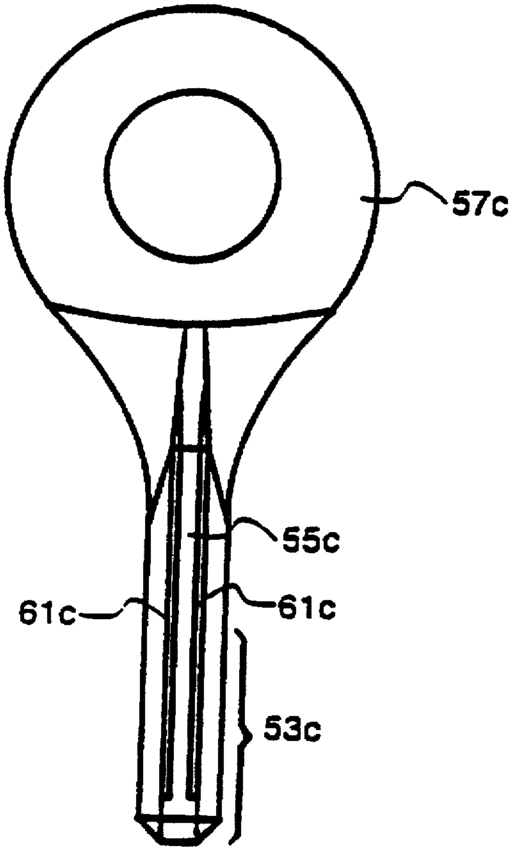

FIGS. 2A, 2B, and 2C show three alternative embodiments of the present invention. In all embodiments, the receiver attachment is integral with the support member, and is coupled to a concha stabilizer pad. In the embodiment of FIG. 2A the receiver attachment comprises curved members **51*a* which are dimensioned to curve around the body of the receiver 27. The curved members 51*a* have retaining members 53*a* which engage the underside of the receiver 27 in holes adapted to receive such retaining members 53*a*, thereby securing the curved members 51*a* to the receiver 27. Integral with, and coupling between the curved members 51*a*, is a curved support arch 55*a* which extends upwards and away from the receiver 27. The top portion 59*a* of the support arch 55*a* is coupled to a concha stabilizer pad 57*a***, which functions as described above.

FIG. 2B shows another alternative embodiment in which the receiver attachment is formed with only retaining members **53*b* for mounting in holes in the upper surface of the receiver 27 adapted to receive such retaining members 53*b*. Integral with, and coupling between the retaining members 53*b*, is a curved support arch 55*b* which extends upward and away from the receiver 27. The top portion 59*b* of the support arch 55*b* is coupled to a concha stabilizer pad 57*b***, which functions as described above.

In the embodiments of FIGS. 2A and 2B the support arch 55 provides the support for the concha stabilizer pad 57, and provides sufficient tension to maintain the concha stabilizer pad 57 against the upper concha 43 during use. In these embodiments the arch 55 and its integral portions 59 and members 53, 55 can be formed of wire, an elastomeric compound, or the like.

FIG. 2C shows another alternative embodiment in which the receiver attachment comprises the end portion **53*c* of a compressed foam support stalk 55*c*, which can be also made of a rigid plastic material. Along the length of the support stalk 55*c* are support ribs 61*c* which increase the rigidity and durability of the support stalk 55*c*. The end portion 53*c* is inserted into a hole in the upper surface of the receiver 27 dimensioned to receiver the support stalk 55*c*. At the opposing end of the support stalk 55*c* is coupled a toriod shaped concha stabilizer pad 57*c* formed of open cell foam, of the type described above. The toriod shape of the concha stabilizer pad 57*c*** enables the pad to deform and adapt to the shape of the upper concha, thereby maintaining the receiver in position.

Figure 3:
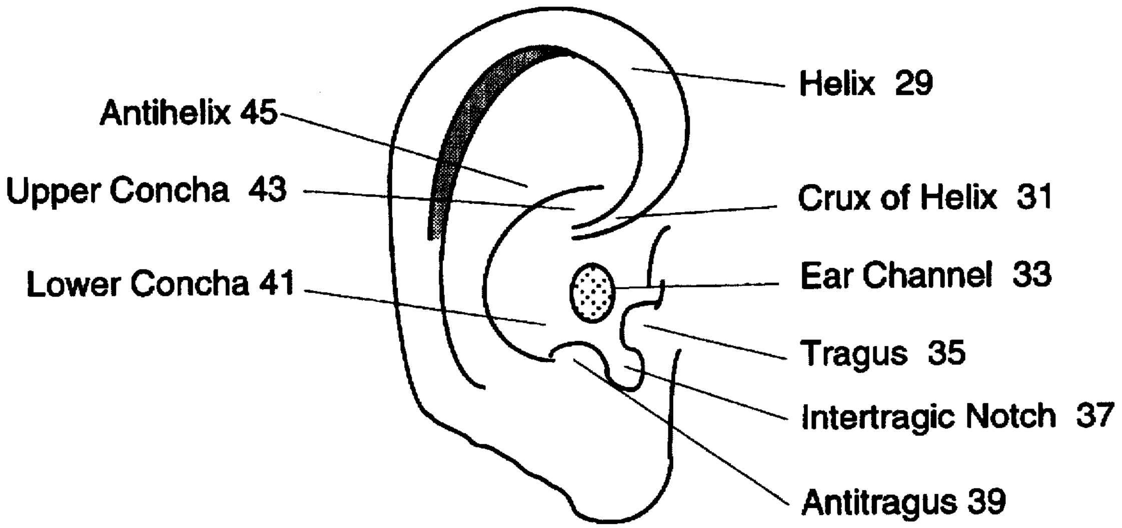
FIG. 3 is a pictorial illustration of the human ear, as described in the Appendix.

FIG. 3 shows a typical human ear. The outer ear, or pinna, is an irregularly concave cartilaginous member comprised of a number of eminences and depressions which give each ear a distinct shape and form. The helix 29 is the curved outer rim of the ear; below the helix 29 is the antihelix 45, a curved prominence which describes a curve around the concha, a deep cavity containing the entry to the ear canal 33. The concha is divided into two parts, the upper and lower concha 41, 43, by the crux of the helix 31 which curves around the outside of the ear, and extends inwards at about the vertical midpoint of the ear. The upper concha 43 lies above the crux of the helix 31 and below the anti-helix 45; the lower concha 41 lies below the crux of the helix 31 and surrounds the entry to the ear canal 33. In front of the lower concha 41 and projecting backwards from the front of the ear is the tragus, 35 a small semicircular prominence. Opposite the tragus 35 and separated from it by the deep curvature of the intertragic notch 37 is the antitragus 39.

The spirit and scope of the invention is not intended to be limited to the description of the preferred embodiment herein, but is capable of use in other environments or combinations, and is capable of modification or changes within the details of the inventive concept described above.

The invention can be used with any concha style headset receiver coupled to any audio source. The headset stabilizer can be used with any headset for personal listening to any audio source device. For example, the invention can be used with headsets typically employed for listening to music, and particularly to headsets used with portable cassette compact disk players radios. Accordingly, the invention is limited only by the claims included herein.

We claim:

1. An apparatus for stabilizing a headset including a receiver sized to fit between a tragus and an anti-tragus of an ear, the apparatus comprising:

an ear cushion dimensioned to cover a portion of the receiver disposed between the tragus and the anti-tragus;

a resilient and flexible stabilizer support member coupled to the ear cushion, and dimensioned to fit within an upper concha with the ear cushion coupled to the receiver and the receiver disposed between the tragus and the anti-tragus; and, a concha stabilizer pad coupled to the stabilizer support member, for contacting the upper concha.

2. The apparatus of claim 1 wherein the ear cushion includes open cell foam.

3. The apparatus of claim 1 wherein the concha stabilizer pad includes compressed open cell foam.

4. The apparatus of the claim 1 wherein the stabilizer support member comprises:

a foam member extending distally between an upper surface of the ear cushion and the concha stabilizer pad.

5. The apparatus of claim 4 further comprising:

at least one support rib extending from the upper surface of the ear cushion along a surface of the foam member to the concha stabilizer pad.

6. The apparatus of claim 1, wherein the concha stabilizer pad is substantially ellipsoid in shape.

7. The apparatus of claim 1, wherein the ear cushion covers a portion of the receiver facing an auditory meatus as the receiver is disposed between the tragus and the anti-tragus.

8. An apparatus for stabilizing a headset including a receiver sized to fit between a tragus and an anti-tragus of an ear, the apparatus comprising:

an ear cushion dimensioned to cover a portion of the receiver disposed between the tragus and the anti-tragus;

a flexible support member extending from an upper surface of the ear cushion towards an upper concha of the ear; and a concha stabilizer pad coupled to the support member at a hinge point for flexing the concha stabilizer pad toward the support member, and having a concha contact point for resting against the upper concha, the support member capable of bending at the hinge point to conform to a size and shape of the upper concha.

9. The apparatus of claim 8 comprising at least one support rib extending from an upper surface of the ear cushion along a surface of the support member to the concha stabilizer pad.

10. A headset comprising:

a receiver sized to fit between a tragus and an antitragus of an ear, the receiver having a tragus contact point, and an anti-tragus contact point disposed substantially opposite to the tragus contact point;

an ear cushion dimensioned to cover a portion of the receiver; and a concha stabilizer coupled to the ear cushion and dimensioned to contact an upper concha between an antihelix and a crux of a helix with the receiver disposed between the tragus and the antitragus.

11. The headset of claim 10 wherein the ear cushion covers a portion of the receiver facing the auditory meatus and the concha stabilizer comprises:

a stabilizer support coupled to the ear cushion and extending toward the upper concha; and a concha stabilizer pad coupled to the stabilizer support, for engaging the upper concha between the antihelix and the crux of the helix for stabilizing the receiver in the ear.

12. An apparatus for stabilizing a headset including a receiver, the apparatus comprising:

an ear cushion that couples to the receiver of the headset, the ear cushion dimensioned to fit in a lower concha between a tragus, and an anti-tragus;

a first, substantially ellipsoid member disposed within a upper concha between an antihelix and a crux of a helix; and, a resilient, flexible second member integrally coupled between the ear cushion and the first member, to maintain the first member within the upper concha.

13. The apparatus of claim 12 wherein the ear cushion is dimensioned to cover a portion of the receiver facing the auditory meatus as the receiver is disposed between the tragus and the anti-tragus.

14. The apparatus of claim 12 further comprising:

at least one support rib extending from the ear cushion along a surface of the second member to a bottom portion of the first member to stiffen the second member.

15. The apparatus of claim 12, wherein:

the first member couples to the second member at a hinge point enabling the first member to flex toward the second member, the first member further including a first contact point that contacts the upper concha between the antihelix and the crux of the helix, the second member bending at the hinge point in response to pressure from the upper concha on the first contact point to conform the second member to a size and shape of the upper concha.

* * * * *

US005712453C1

(12) EX PARTE REEXAMINATION CERTIFICATE (8055th)

United States Patent

Bungardt et al.

(10) Number: US 5,712,453 C1

(45) Certificate Issued: Mar. 1, 2011

(54) CONCHA HEADSET STABILIZER

(75) Inventors: Gabriele Bungardt, Aptos, CA (US); Luis Pedraza, Hyde Park, MA (US); Betsy Goodrich, Roslindale, MA (US); Edmund J. Morrissey, III, Aptos, CA (US)

(73) Assignee: Plantronics, Inc., Santa Cruz, CA (US)

Reexamination Request:
No. 90/010,731, Nov. 9, 2009

Reexamination Certificate for:

| | |
|---|---|
| Patent No.: | **5,712,453** |
| Issued: | **Jan. 27, 1998** |
| Appl. No.: | **08/420,241** |
| Filed: | **Apr. 11, 1995** |

Related U.S. Application Data

(63) Continuation of application No. 08/234,302, filed on Apr. 28, 1994, now abandoned.

(51) Int. Cl.
*H04R 1/10* (2006.01)

(52) U.S. Cl. ........................................ 181/135; 381/385

(58) Field of Classification Search ........................ None
See application file for complete search history.

(56) References Cited

U.S. PATENT DOCUMENTS

| | | | |
|---|---|---|---|
| 1,668,890 | A | 5/1928 | Curran et al. |
| 1,753,817 | A | 4/1930 | Aber |
| 1,852,130 | A | 4/1932 | Schier |
| 1,893,143 | A | 1/1933 | Koch |
| 1,893,474 | A | 1/1933 | Lieber |
| 1,969,559 | A | 8/1934 | Kelly |
| 2,312,534 | A | 3/1943 | Fiene |
| 2,487,038 | A | 11/1949 | Baum |
| 2,535,258 | A | 12/1950 | Bland |
| 2,595,489 | A | 5/1952 | Rutter et al. |
| 2,738,850 | A | 3/1956 | Tooker |
| 2,763,334 | A | 9/1956 | Starkey |
| 2,808,468 | A | 10/1957 | Knauert |
| 2,904,640 | A | 9/1959 | Dreher et al. |
| 2,908,343 | A | 10/1959 | Hummert |

(Continued)

FOREIGN PATENT DOCUMENTS

| | | |
|---|---|---|
| EP | 0010168 | 4/1980 |
| EP | 0010169 | 4/1980 |
| GB | 1179692 | 1/1970 |
| GB | 1297914 | 11/1972 |
| JP | S2-3410 | 8/1927 |

(Continued)

OTHER PUBLICATIONS

Hearing Instruments, "Memory Form Earmold Kit", May 1983, vol. 34, No. 5, p. 43.

(Continued)

*Primary Examiner*—James Menefee

(57) ABSTRACT

An apparatus for stabilizing a concha style headset comprises a receiver attachment that couples to the body of the receiver of the headset, a flexible and resilient support member extending from the receiver attachment, and a concha stabilizer pad coupled to the end of the support member, such that the concha stabilizer pad contacts the upper concha under the antihelix of the ear with the receiver placed in the lower concha in front of the ear canal. The receiver attachment can include a foam ear cushion that covers the portion of the receiver that is placed in the lower concha, with the concha stabilizer pad and the flexible support member formed of a compressed cellular foam. Support ribs extend from the upper surface of the ear cushion along the surface of the support member and join the concha stabilizer pad. Alternatively, the receiver attachment can include retaining members that engage in mounting holes in the receiver, and may include curved members which wrap around the body of the receiver when the retaining members mount the underside of the receiver. The support member can then include a flexible arch or stalk, with the concha stabilizer pad (or torus) located at the top of the arch.

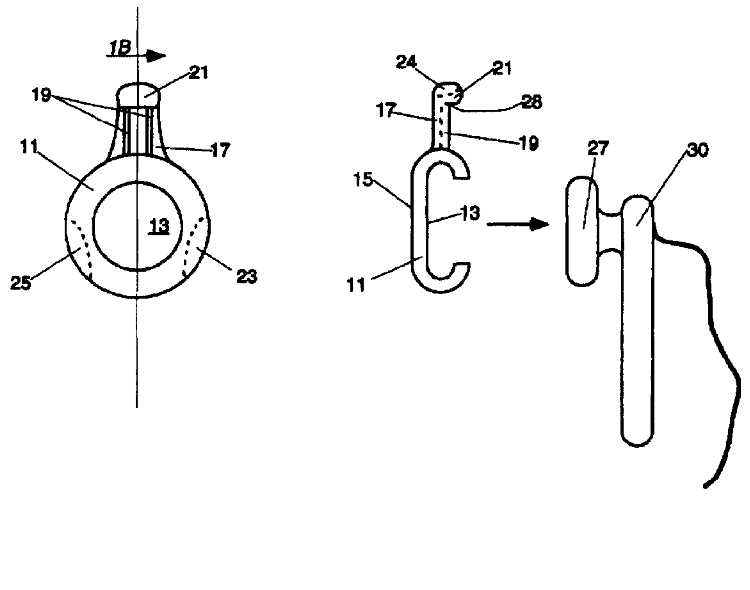

U.S. PATENT DOCUMENTS

| | | | |
|---|---|---|---|
| 2,939,923 | A | 6/1960 | Henderson |
| 2,971,065 | A | 2/1961 | Busse |
| 3,097,059 | A | 7/1963 | Hoffman |
| 3,170,046 | A | 2/1965 | Leale |
| 3,258,533 | A | 6/1966 | Bredon |
| 3,345,737 | A | 10/1967 | Gordon |
| 3,440,365 | A | 4/1969 | Bryant et al. |
| 3,496,306 | A | 2/1970 | Pollak |
| 3,865,998 | A | 2/1975 | Weiss et al. |
| 4,069,400 | A | 1/1978 | Johanson et al. |
| 4,091,067 | A | 5/1978 | Kramer et al. |
| D266,271 | S | 9/1982 | Johanson et al. |
| 4,375,016 | A | 2/1983 | Harada |
| 4,403,120 | A | 9/1983 | Yoshimi |
| 4,420,657 | A | 12/1983 | Larkin |
| 4,443,668 | A | 4/1984 | Warren |
| 4,587,965 | A | 5/1986 | de Boer et al. |
| 4,720,857 | A | 1/1988 | Burris et al. |
| 4,736,435 | A | 4/1988 | Yokoyama et al. |
| 4,821,247 | A | 4/1989 | Grooms |
| 4,965,838 | A | 10/1990 | Kamon et al. |
| 4,972,492 | A | 11/1990 | Tanaka et al. |
| D318,473 | S | 7/1991 | Miyashita et al. |
| 5,048,090 | A | 9/1991 | Geers |
| D337,118 | S | 7/1993 | Seikita |
| D338,530 | S | 8/1993 | Oberlander |
| 5,247,946 | A | 9/1993 | Holder |
| 5,298,692 | A | 3/1994 | Ikeda et al. |
| 5,319,163 | A | 6/1994 | Scott |
| 5,357,576 | A | 10/1994 | Arndt |
| D353,379 | S | 12/1994 | Nakamura et al. |
| D367,113 | S | 2/1996 | Weeks |
| D371,368 | S | 7/1996 | Hayashi |
| 5,544,253 | A | 8/1996 | Nagayoshi et al. |
| 5,659,156 | A | 8/1997 | Mauney et al. |
| 5,949,891 | A | 9/1999 | Wagner et al. |

FOREIGN PATENT DOCUMENTS

| | | |
|---|---|---|
| JP | 58-104077 | 7/1983 |
| JP | 60-89765 | 6/1985 |
| JP | H4-149 | 7/1985 |
| JP | H2-278998 | 11/1990 |
| JP | H4-233398 | 8/1992 |
| JP | H4-233400 | 8/1992 |

OTHER PUBLICATIONS

Hearing Instruments, “Doc’s Promold”, Jan. 1989, vol. 40, No. 1 p. 48.

Hearing Instruments, “Doc’s Promold”, Mar. 1989, vol. 40, No. 3, p. 40.

Hearing Instruments, “Doc’s Promold”, Aug. 1990, vol. 41, No. 8, p. 18.

Hearing Instruments, “Sensaphonics”, Feb. 1994, vol. 45, No. 2, p. 24.

J.L. Sheehy et al., “Doc’s Proplugs”, Otolaryngolgoy—Head and Neck Surgery, Feb. 1983, vol. 91, No. 1, pp. 94–95.

M. Tate, “Principles of Hearing Aid Audiology”, 1994, pp. 127, 178–181. Chapman & Hall.

Michael Okuda, Denise Okuda, and Debbie Mirek, The Star Trek Encyclopedia: A Reference Guide to the Future, p. 84, 1994, Pocket Books, a division of Simon & Schuster Inc.

S. Cargill et al., “Strategies for fitting FM units to children with unilateral hearing losses”, Hearing Instruments, Jul. 1991, vol. 42, No. 7, pp. 26–27.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1, 7, 10 and 11 is confirmed.

New claims 16-56 are added and determined to be patentable.

Claims 2-6, 8, 9 and 12-15 were not reexamined.

*16. The headset of claim 10, wherein the concha stabilizer is adapted to remain stationary with respect to the receiver with a concha stabilizer axis aligned with a longitudinal axis of the headset.*

*17. The headset of claim 10, wherein the concha stabilizer automatically adjusts to a proper position within the upper concha.*

*18. The headset of claim 10, wherein the concha stabilizer is formed from a non-metallic material.*

*19. The headset of claim 18, wherein the non-metallic material is a foam material.*

*20. The headset of claim 10, wherein the ear cushion is adapted to remain stationary with respect to the receiver while the receiver is inserted in a user ear during use.*

*21. The apparatus of claim 1, wherein the ear cushion, the resilient and flexible stabilizer support member, and the concha stabilizer pad are formed from a same material.*

*22. The headset of claim 21, wherein the same material is foam.*

*23. The headset of claim 20, wherein an axis of the concha stabilizer is aligned with a headset longitudinal axis while the ear cushion is attached to the headset receiver.*

*24. The headset of claim 20, wherein the concha stabilizer automatically adjusts to a proper position within the upper concha.*

*25. The headset of claim 20, wherein the concha stabilizer is substantially toroid shaped.*

*26. The headset of claim 10, wherein the concha stabilizer is adapted to self adjust to a proper position within the upper concha beneath the antihelix, and wherein the concha stabilizer is formed from a same material forming the ear cushion.*

*27. The headset of claim 26, wherein an axis of the concha stabilizer is aligned with a headset longitudinal axis while the ear cushion is attached to the receiver.*

*28. The headset of claim 26, wherein the same material is a non-metallic material.*

*29. The headset of claim 26, wherein the concha stabilizer comprises a toroid.*

*30. The apparatus of claim 1, wherein the ear cushion, the resilient and flexible stabilizer support member, and the concha stabilizer pad are a single piece.*

*31. The headset of claim 10, wherein the concha stabilizer has an opening.*

*32. The headset of claim 31, wherein the opening facilitates the concha stabilizer deforming and adapting to a shape of the upper concha.*

*33. The headset of claim 10, wherein the concha stabilizer has a vacant center.*

*34. The headset of claim 33, wherein the vacant center facilitates the concha stabilizer deforming and adapting to a shape of the upper concha.*

*35. The headset of claim 10, wherein at least a portion of the concha stabilizer is torus shaped.*

*36. The headset of claim 35, wherein the portion of the concha stabilizer which is torus shaped facilitates the concha stabilizer deforming and adapting to a shape of the upper concha.*

*37. The headset of claim 10, wherein at least a portion of the concha stabilizer is ring shaped.*

*38. The headset of claim 37, wherein the ring shaped portion of the concha stabilizer facilitates the concha stabilizer deforming and adapting to a shape of the upper concha.*

*39. The headset of claim 10, wherein the concha stabilizer is substantially torus shaped.*

*40. The headset of claim 39, wherein the substantially torus shape facilitates the concha stabilizer deforming and adapting to a shape of the upper concha.*

*41. The headset of claim 10, wherein the concha stabilizer is substantially ring shaped.*

*42. The headset of claim 41, wherein the substantially ringed shape facilitates the concha stabilizer deforming and adapting to a shape of the upper concha.*

*43. The headset of claim 10, wherein the concha stabilizer is adapted for a deformation and adaptation to a shape of an upper concha.*

*44. The headset of claim 43, wherein a concha stabilizer shape of the concha stabilizer facilitates the deformation and adaptation to the shape of the upper concha.*

*45. The headset of claim 44, wherein the concha stabilizer shape has an opening.*

*46. The headset of claim 44, wherein the concha stabilizer shape has a vacant center.*

*47. The headset of claim 44, wherein the concha stabilizer shape comprises a torus shaped portion.*

*48. The headset of claim 44, wherein the concha stabilizer shape comprises a ring-shaped portion.*

*49. The headset of claim 44, wherein the concha stabilizer shape is substantially torus shaped.*

*50. The headset of claim 44, wherein the concha stabilizer shape is substantially ring shaped.*

*51. The headset of claim 43, wherein the deformation and adaptation of the concha stabilizer to the shape of the upper concha is facilitated by an opening in the concha stabilizer.*

*52. The headset of claim 43, wherein the deformation and adaptation of the concha stabilizer to the shape of the upper concha is facilitated by a vacant center of the concha stabilizer.*

*53. The headset of claim 43, wherein the deformation and adaptation of the concha stabilizer to the shape of the upper concha is facilitated by at least a portion of the concha stabilizer that is torus shaped.*

*54. The headset of claim 43, wherein the deformation and adaptation of the concha stabilizer to the shape of the upper concha is facilitated by at least a portion of the concha stabilizer that is ring shaped.*

*55. The headset of claim 43, wherein the deformation and adaptation of the concha stabilizer to the shape of the upper concha is facilitated by a substantially torus shape of the concha stabilizer.*

*56. The headset of claim 43, wherein the deformation and adaptation of the concha stabilizer to the shape of the upper concha is facilitated by a substantially ringed shape of the concha stabilizer.*

* * * * *